(12) United States Patent
Haskell et al.

(10) Patent No.: US 8,145,506 B2
(45) Date of Patent: Mar. 27, 2012

(54) PATIENT PROBLEM DATA STRUCTURE AND PROCESSING SYSTEM

(75) Inventors: Robert Emmons Haskell, Chester Springs, PA (US); Susan Annette Matney, Woods Cross, UT (US); Carmela Anne Couderc, West Chester, PA (US); Mary Ellen Dlugos, King of Prussia, PA (US); Rebecca Rae DaDamio, Sinking Spring, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 386 days.

(21) Appl. No.: 12/433,500

(22) Filed: Apr. 30, 2009

(65) Prior Publication Data

US 2009/0276240 A1    Nov. 5, 2009

Related U.S. Application Data

(60) Provisional application No. 61/049,471, filed on May 1, 2008.

(51) Int. Cl.
*G06Q 50/00* (2006.01)
(52) U.S. Cl. .............................. 705/3; 705/2
(58) Field of Classification Search ................ 705/2–3; 700/100; 600/300; 707/104.1
See application file for complete search history.

(56) References Cited

U.S. PATENT DOCUMENTS

| | | | |
|---|---|---|---|
| 6,272,481 B1 | 8/2001 | Lawrence et al. | |
| 6,401,072 B1 | 6/2002 | Haudenschild et al. | |
| 7,747,392 B2 * | 6/2010 | Ruano et al. | 702/19 |
| 7,925,603 B1 * | 4/2011 | Laidig et al. | 706/45 |
| 2006/0167721 A1 | 7/2006 | Bernard et al. | |
| 2007/0244723 A1 | 10/2007 | Nagaeda | |
| 2008/0086336 A1 | 4/2008 | Hertel et al. | |
| 2010/0324925 A1 * | 12/2010 | Barkan et al. | 705/2 |

OTHER PUBLICATIONS

The International Organization for Standardization, Health Informatics—Integration of a reference terminology model for nursing (ISO 18104:2003); German version EN ISO 18104:2003, text in English. International Classification of Nursing Practice, ICNP Version 1.0 Book, Chapter 2—INCP Development, 2005, place Jean-Marteau, 1201 Geneva (Switzerland).

* cited by examiner

*Primary Examiner* — Luke Gilligan
(74) *Attorney, Agent, or Firm* — Alexander J Burke

(57) ABSTRACT

A patient problem data system stores data representing a plurality of different patient problems for use in providing healthcare to a patient. An acquisition processor acquires data representing a patient problem for storage in a repository. A repository, electrically coupled to the acquisition processor, includes data representing a plurality of different patient problems; an individual patient problem has a patient problem name and is characterized by patient problem attributes; an individual patient problem has a plurality of attribute properties determining how a patient problem attribute is represented. Patient problem attributes include a focus term indicating a topic of a patient problem, a patient problem likelihood term indicating an assessment of likelihood of the associated corresponding patient problem, and a client term indicating at least one target person for care. The attribute properties include a format attribute property indicating a format constraint of a patient problem attribute and a content attribute property indicating a content constraint of a patient problem attribute. A retrieval processor, electrically coupled to the repository, retrieves data representing at least one patient problem from the repository.

24 Claims, 14 Drawing Sheets

PATIENT PROBLEM DATA STRUCTURE AND PROCESSING SYSTEM

This is a Non-provisional patent application that claims priority from U.S. Provisional Patent Application Ser. No. 61/049,471 filed on May 1, 2008 by Robert Haskell et al.

FIELD OF THE INVENTION

The invention concerns a standardized patient problem data structure and processing system for use in providing healthcare to a patient population.

BACKGROUND OF THE INVENTION

There are multiple clinical terminologies in the healthcare industry in use. Each different set of clinical terms are associated with a set of pre-coordinated, free text patient problems. These sets of patient problems are further associated with their own either implicit or explicit terminology models. A problem arises when different participants in the healthcare industry want to communicate with one another. Generally, the problems in one healthcare system can neither be understood nor mapped for use by a second different healthcare system in any objective way, except through communication between problem terminology developers associated with their respective healthcare system. These developers understand the meaning of their own patient problems. However, even then, direct equivalence is often not possible.

While, Healthcare Information Technology (HIT) systems may use these terminologies, these systems do not utilize a model-based implementation. The international nursing informatics community has supported the development of models describing patient diagnoses and clinical actions. These models are described by the International Organization of Standards (ISO) in document ISO 18104:2003. The International Council of Nurses (ICN) conforms to these ISO nursing models with the International Classification of Nursing Practice (ICNP), which is described as a 7 Axis Model in ICNP Version 1.0 (see http://www.icn.ch/icnp.htm). Deficiencies associated with known systems include:

Patient diagnoses/problems which are not sufficiently described to enable their use within an operational HIT solution, such as an interdisciplinary plan of care application. Publicly available industry models have insufficient specificity of detailed attributes to fully support application requirements and insufficient supporting attribute properties to define application and user interface behavior.

Inability, by HIT systems, to decompose problems into a consistent, unambiguous, and computable definition, which enables secondary data use based on specific problem characteristics. Simple text expression of a Patient problem is insufficient to support optimizing clinical practice for individual patients at the point of care, as well as managing clinical outcomes for patient behavior in the aggregate.

Thus, in known systems, data is not easily shared across systems that do not use common and semantically consistent definitions. These systems do not include standard models to help promote consistent data usage across a healthcare enterprise or different enterprises. A system according to invention principles addresses these deficiencies and related problems.

BRIEF SUMMARY OF THE INVENTION

A patient problem data system stores data representing a plurality of different patient problems for use in providing healthcare to a patient. An acquisition processor acquires data representing a patient problem for storage in a repository. A patient problem is a human condition needing treatment or management. A repository, electrically coupled to the acquisition processor, includes data representing a plurality of different patient problems; an individual problem has a problem name and is characterized by problem attributes; an individual problem attribute has a plurality of attribute properties determining how a problem attribute is represented. The problem attributes include a focus term indicating a topic of the patient problem, a patient problem likelihood term indicating an assessment of likelihood of the associated corresponding patient problem, and a client term indicating at least one target person for care. The attribute properties include a format attribute property indicating a format constraint of a problem attribute and a content attribute property indicating a content constraint of a problem attribute. A retrieval processor, electrically coupled to the repository, retrieves data representing at least one patient problem from the repository.

BRIEF DESCRIPTION OF THE DRAWING

FIG. 8 is a block diagram showing a second example of a patient problem name according to invention principles; and.

DETAILED DESCRIPTION OF THE INVENTION

Patient Problem Data System 10 (FIG. 1) provides a model data structure that uses detailed attributes within each individual model, to facilitate consistent data collection, storage, and processing of patient problem phrases. A patient problem may be characterized as a nursing problem or medical problem. The model identifies attributes that define a clinical patient problem in a form that can be used within any information system. The attributes are collected and standardized to advantageously allow system 10 to provide a model that can be used in multiple different clinical applications. One particular set of attribute properties associated with a patient problem phrase exists for each clinical application. As a result, system 10 provides a standardized universal model that is the same across all clinical applications, yet provides the flexibility for the use of the model to differ between each clinical application. As will be discussed hereinbelow, the model-driven functionality of system 10 decomposes patient problems into consistent, unambiguous, and computable definitions that facilitate efficient and consistent data sharing across a multitude of information systems, throughout and between different healthcare enterprises.

Figure 1:
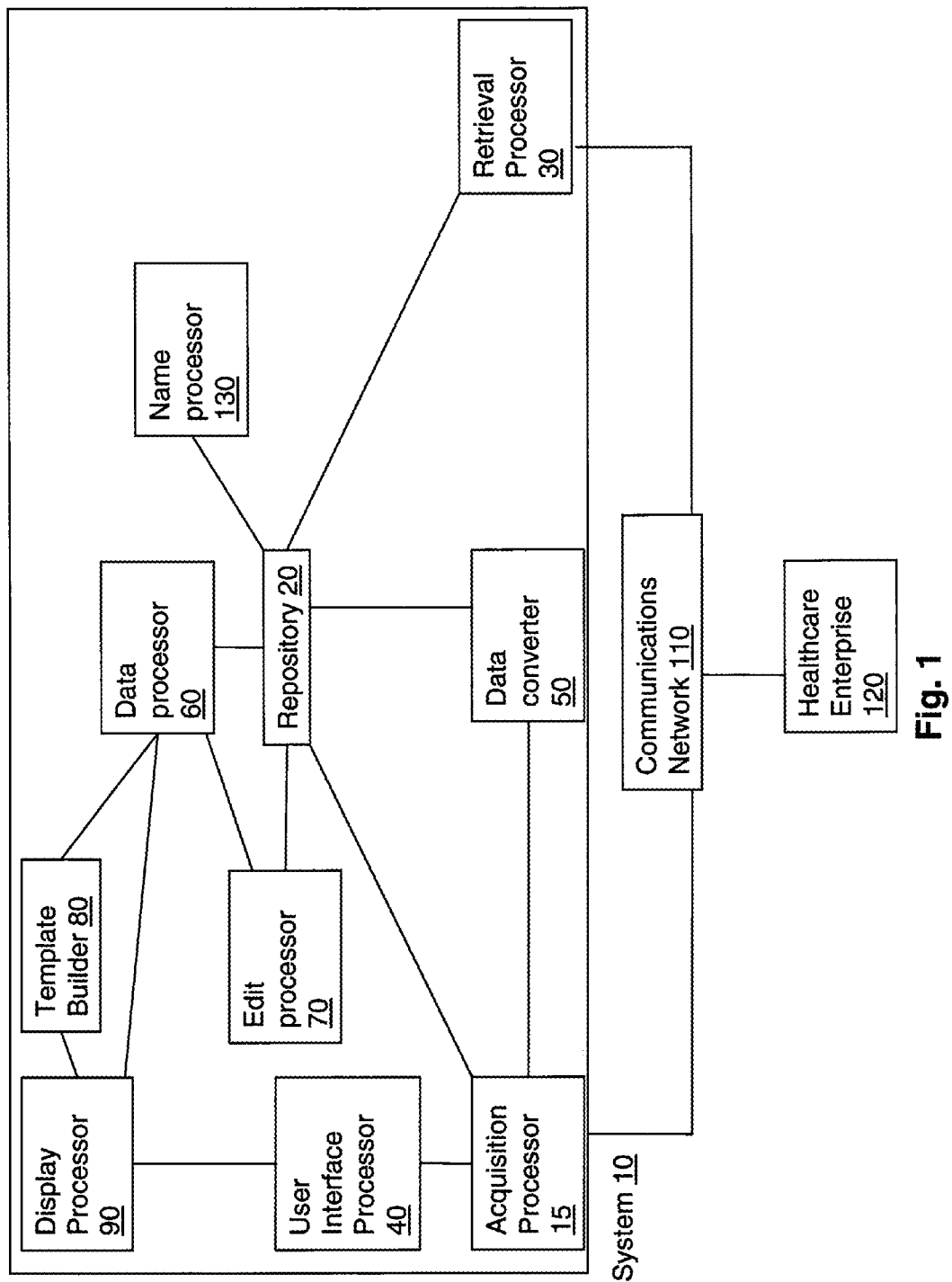
FIG. 1 is a block diagram of the system for providing a patient care and treatment data structure and processing according to invention principles.

A block diagram for a system for storing and processing data structures related to providing healthcare to a patient is shown in FIG. 1. An executable application, as used herein, comprises code or machine readable instructions for conditioning a processor to implement predetermined functions, such as those of an operating system, a context acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

A user interface (UI), as used herein, comprises one or more display images, generated by a display processor and enabling user interaction with a processor or other device and associated data acquisition and processing functions. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application manipulates the UI display images in response to the signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure. A document or record comprises a compilation of data in electronic or paper form.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams. A document or record comprises a compilation of data in electronic form and is the equivalent of a paper document and may comprise a single, self-contained unit of information.

A repository 20 stores data including data representing a plurality of different patient problems. An individual patient problem is defined as a human condition needing treatment or management. A problem may be one of the following: patient diagnosis, sign or symptom, finding, or risk factor. Each individual patient problem has a problem name that is characterized by problem attributes. A patient problem name is a statement, such as Gas Exchange Impairment or Pain Risk, which is defined by the individual combination of associated patient problem attribute values. As a result, an individual problem name may be standardized to be consistently constructed with a given set of problem attributes. The problem attributes includes a focus term to describe the topic of the patient problem, a patient problem likelihood term to indicate an assessment of the likelihood of the associated corresponding patient problem, a client term to describe at least one target of care, and a judgment term to describe the clinical opinion or determination about the actual or potential health problem, which are described below in connection with FIGS. 5A-5F. The judgment term may indicate a positive state (e.g., increase), negative (e.g., impairment), or neutral state (e.g., not valued). Additional problem attributes which may be utilized are: (a) time (which is derived from one or more of the following attributes: condition acuity, chronologic developmental stage, event, time pattern), (b) severity, and (c) location. These additional patient problem attributes are described below and shown in FIG. 6. The problem attributes may also include an indication of review action and an indication of approval action needed in the treatment of a patient condition.

Problem attributes are characterized by attribute properties which determine how a problem attribute is represented or used in conjunction with a particular clinical application. An individual application in communication with System 10 uses its own individual attribute properties to account for behavior differences and constraints within a particular clinical application's user interface characteristics. Attribute properties include a format attribute property, a content attribute property, and a processing attribute property. Format attribute property indicates a format constraint of a problem attribute which dictates how a particular problem attribute is formatted or presented. Format constraints include at least one of: (a) maximum character length of an attribute, (b) unit of measure of an attribute, and, (c) number of decimal places an attribute has. Format constraints may have default values that are selectively assignable by a user. A content attribute property is a content constraint of a problem attribute, which dictates how a particular problem attribute may be modified. Content constraints include at least two of: (a) an allowable value set of an attribute, (b) a default value of an attribute, (c) a maximum number of values allowed for an attribute, and (d) an indication that free text entry is allowable for user entry of data representing an attribute. Processing attributes are parameters which provide information on how a particular problem attribute is to be edited, used, or displayed. Processing attributes are composed of properties including at least one of: (a) an indication an attribute is to be processed in performing a check for a duplicate problem, (b) an indication a default value is required for an attribute, (c) an indication an attribute is required for use by an executable clinical application, (d) an indication an attribute is displayed in a display image associated with an executable clinical application, and (e) an indication an attribute value may be overridden.

Repository 20 further includes metadata attributes associated with a particular patient problem. Meta data attributes include at least one of: (a) a problem identifier, (b) external references, (c) synonyms, and (d) data identifying who created, changed, or reviewed patient problem information, which are associated with an individual patient problem. Metadata attributes are defined as common concepts to the patient problem model which further define a problem attribute. These attributes contain administrative and supplemental information to further describe the model.

System 10 also includes an acquisition processor 15, electrically coupled to repository 20 and communications network 110. Processor 15 is conditioned for acquiring data representing a patient problem for storage in repository 20. Acquired data is derived from repository 20 or from a remote system in a healthcare enterprise 120 via a communications network 110. Acquired data, in one embodiment, is acquired automatically from a source in response to an initiated executable procedure, through an attribute property driving operation of an individual application, or in response to user input. Acquisition processor 15 is conditioned, in response to executable instruction, to load system 10 with model-based patient problems for use in clinical applications, as well as ensure that the loaded patient problems are compatible with attribute properties for use with those clinical applications.

System 10 further includes retrieval processor 30, electrically coupled to repository 20 and communications network 110 in order to retrieve data representing at least one patient problem from repository 20. Retrieved data may be transmitted for receipt by communications network 110. Acquisition processor 15 and retrieval processor 30 are electrically coupled to communications network 110 to facilitate communication and data transmission between System 10 and healthcare enterprise 120. Healthcare enterprise 120 includes any system within a healthcare information system, for example a clinical information system, workflow system, and financial information system. Healthcare enterprise 120 may include systems that are commonly operated by a single healthcare entity or systems operated by distinctly owned and operating healthcare providers. Data representing a patient problem is bidirectionally communicated between System 10 and enterprise 120. Communication occurs in any of the following instances: (a) when a patient problem is loaded into System 10 or (b) in response to population of attributes of a patient problem for a particular patient problem enabling System 10 to communicate patient problem data for use by at least one clinical application of healthcare enterprise 120.

System 10 includes data converter 50, electrically coupled to repository 20 and acquisition processor 15. Data converter 50 converts data representing a patient problem acquired by acquisition processor 15, automatically or in response to user command, to be compatible with attribute properties stored in repository 20 or attribute properties of a particular clinical application. Data converter 50 facilitates interoperability between different information systems within a healthcare enterprise by providing a common data syntax of attributes that are used by system 10 for translating patient problems into a common format and for driving application operation based on the patient problem data.

User interface processor 40 is electrically coupled to acquisition processor 15 and is conditioned to provide data representing at least one display image including image elements that allow a user to enter patient problem attributes, as well as prompt a user to select corresponding attribute properties. In response to loading of data representing a patient problem, the patient problem data is computationally decomposed into patient problem attributes. These attributes are matched to attributes of an already defined patient problem. If the attributes do not match, a new patient problem is added. User interface processor 40 facilitates the addition of a new patient problem by allowing a user to specify attribute properties for already entered patient problem attributes, or further define patient problem by entering additional patient problem attributes and define their corresponding attribute properties. In addition, user interface processor 40 enables a user to visually organize similar patient problems by providing a display image using user selectable image elements for selecting a plurality of patient problem data instances for inclusion as a set of patient problems. Patient problem set creation is further described with respect to FIG. 6.

Edit processor 70 facilitates efficient changes to data representing patient problems. Edit processor 70, electrically coupled to repository 20 and data processor 60, allows a user to edit data representing a patient problem for storage in repository 20. In certain circumstances, attribute values of patient problems are changed to either create an entirely new patient problem, or alternatively edit the existing patient problem. When patient problem attributes are modified, added, or deleted, the patient problem name may change, which results in an entirely new patient problem name to be added to repository 20. In addition, edit processor 70 facilitates the modification of attribute properties to conform a patient problem to attribute properties specific to particular clinical applications.

System 10 further enables a user to generate data representing a patient problem via template builder processor 80. Template builder processor 80 is electrically coupled to display processor 90 and data processor 60 and allows a user to generate data representing an individual patient problem or a patient problem set comprised of a plurality of individual patient problems. Template builder processor 80 facilitates the changing of patient problem attributes and attribute properties in order to create or modify patient problems. Template builder processor 80 operates under direction of stored executable instructions and provides data to display processor 90 representing display images including at least one user selectable image element enabling a user, via a user interface, to selectively modify patient problem data by adding, deleting, or changing at least one of the attributes and attribute properties associated with at least one patient problem or set of patient problems.

Data processor 60 is electrically coupled to repository 20, display processor 90, edit processor 70, and template builder processor 80. Data processor 60 searches data in repository 20 to identify a particular patient problem in response to user entered data representing attribute properties. Data processor 60 searches repository 20 to identify at least one of: (a) a candidate plan of care, (b) a treatment, and (c) a diagnosis, associated with a particular patient problem in response to user entered data identifying patient problem attributes having certain attribute properties. In response to loading by system 10 of patient problem data, system 10 automatically decomposes patient problem attributes in order to match attributes with patient problem attributes of patient problems already stored in repository 20. Patient problem data includes at least one attribute data field and the at least one attribute data field includes at least one attribute property data field corresponding to a term of the patient problem data. Additionally, as will be discussed with respect to FIGS. 5A-5F, data processor 60 analyzes the order of terms comprising patient problem data to determine if patient problem data already exists on system 10. Attribute data fields and attribute property data fields include different data values corresponding to characteristics that define patient problem data. Data processor 60 automatically decomposes patient problem data by parsing acquired patient problem data to determine a number of attribute data fields and attribute property data fields associated with the identified attribute data fields. Data processor 60 uses data values in attribute fields and attribute property fields and compares the identified data values with attribute data values and/or attribute property data values associated with the particular patient problem model and which are stored in repository 20. Data processor 60 automatically determines if attributes match in order to ascertain that a patient problem is a duplicate and does not need to be added to repository 20 thereby facilitating a consistent model for use by any clinical application or driving operation of a clinical application within a healthcare system.

System 10 includes name processor 130 electrically coupled to repository 20, for automatically allocating a name to a patient problem in response to predetermined naming rules. A patient problem name is generated by name processor 130 based upon patient problem attributes, for example using terms stored in any of judgment attribute, client attribute, focus attribute, and likelihood attribute. The predetermined naming rules used in this case is described below and shown in FIGS. 5A-5F.

Figure 2:
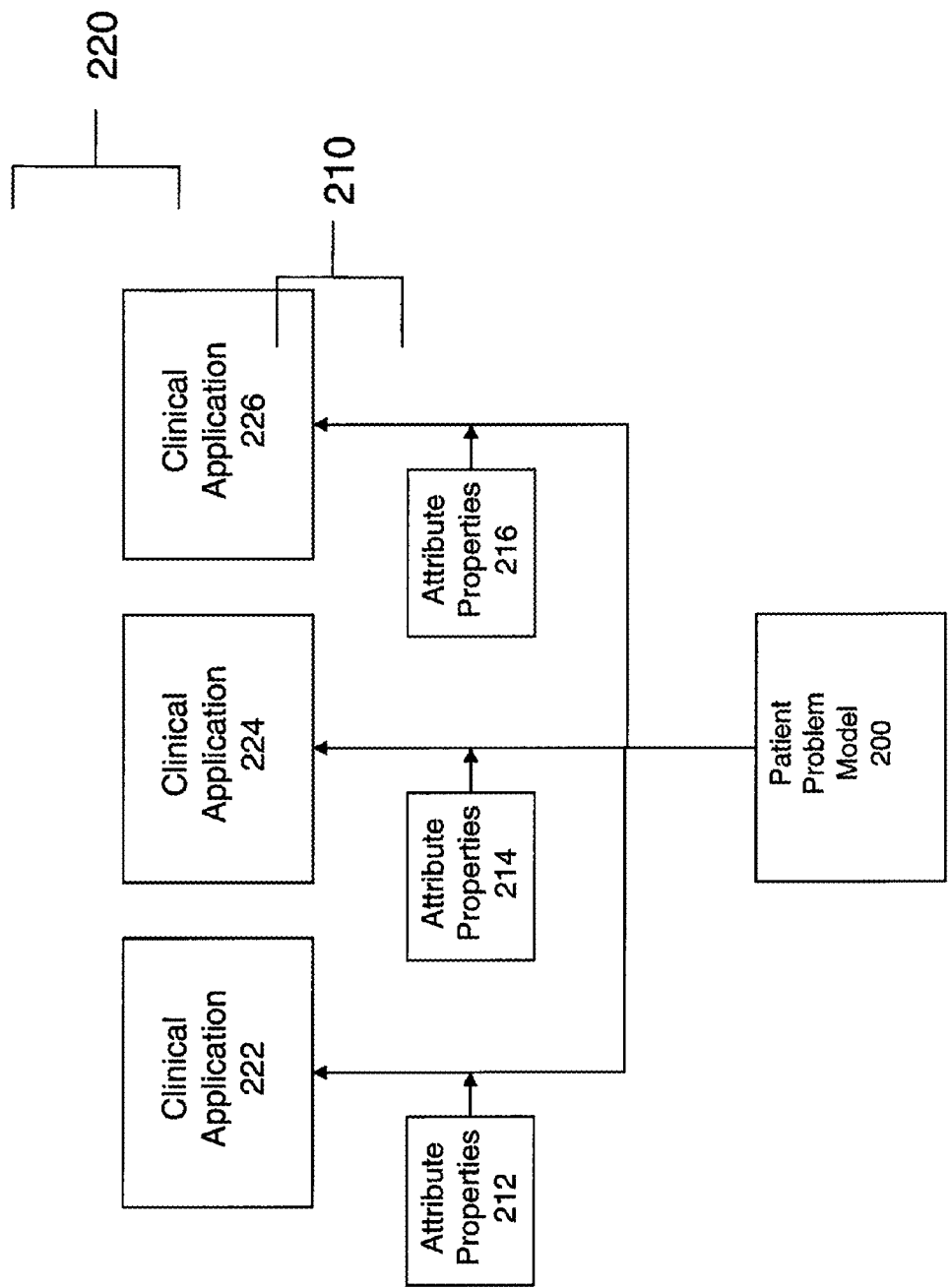
FIG. 2 is a block diagram showing a patient problem model and its interaction with a plurality of clinical applications according to invention principles.

A block diagram showing a patient problem model and its interaction with a plurality of clinical applications is shown in FIG. 2. Patient Problem Model 200 is the common patient problem model stored in repository 20 of system 10. Patient Problem Model 200 is used by a plurality of clinical applications 220. For example, clinical application 222 may be a radiology information system that uses data in model 200 for assigning a task to a particular worker to obtain an image study for a particular patient based on patient problem data. While FIG. 2 illustrates three clinical applications 222, 224, and 226, any number of clinical or other applications that operate in a healthcare enterprise may be in communication with system 10 and able to use model 200 for presenting patient data in a desired manner or causing an application to operate in a specified manner. Model 200 includes data representing patient problems and attribute properties associated with particular patient problem data. Attribute properties 210 are application specific attributes that specify how attributes within Patient Problem Model 200 are used by a particular clinical application. For example, a specific set of attribute properties 212 exist for clinical application 222. Clinical applications parse medical outcome data to determine data values of attribute properties. The data values of attribute properties provide operating instructions to a respective clinical application driving operation of the clinical application or determining the manner in which the clinical application uses the patient problem data. Thus, since attribute properties 212 and 214 will differ since they correspond to clinical application 222 and 224 respectively, the use of Model 200 within clinical application 222 and 224 will likewise differ. As a result, specific attribute properties are available for each patient problem attribute for a particular clinical application to drive the application and determine user interface behavior. System 10 advantageously provides a repository of patient problems that is selectively modifiable and expandable to enable a user to easily set attribute properties associated with a particular patient problem and which are useable by a plurality of different applications in a healthcare system.

Figure 3:
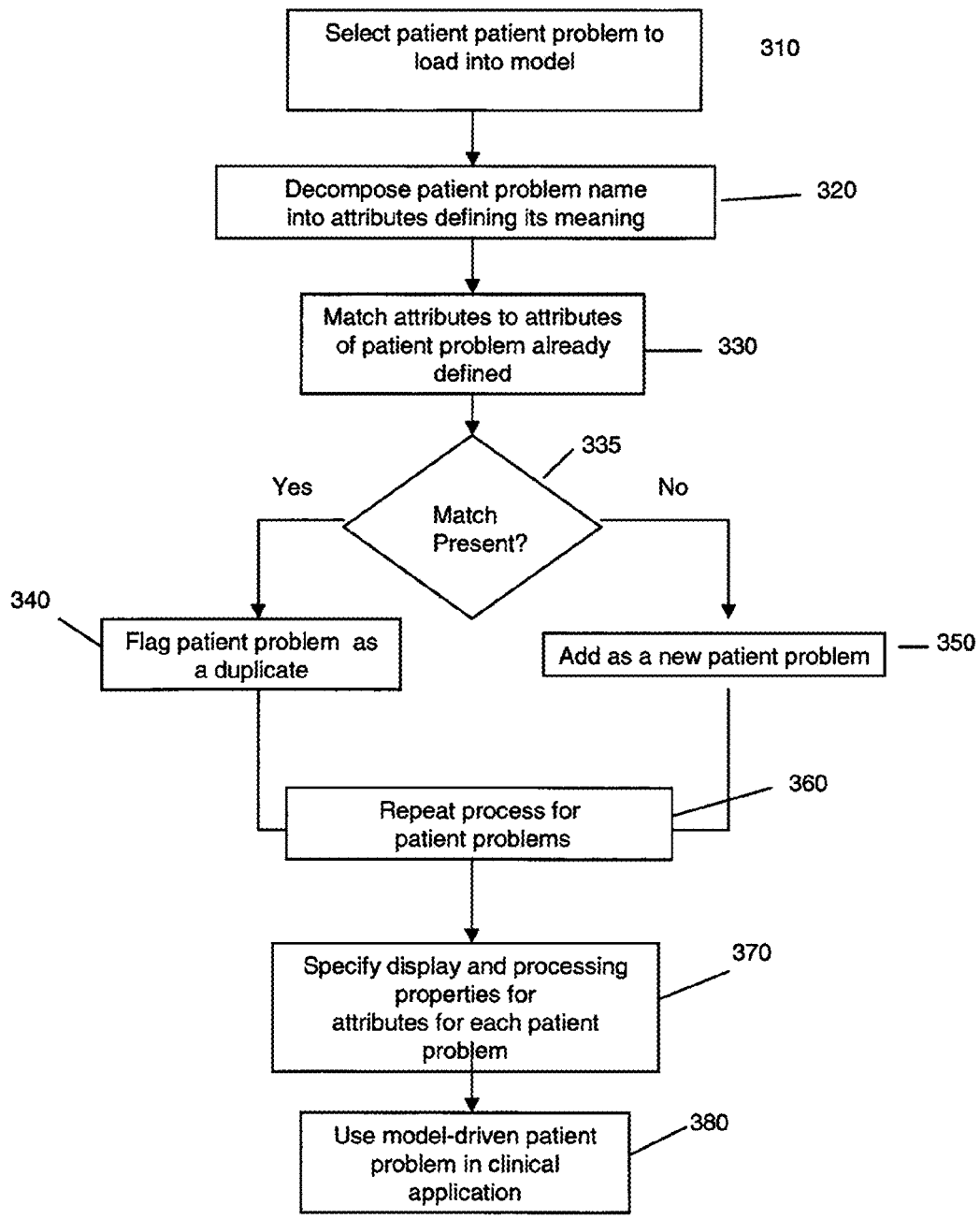
FIG. 3 is a flow diagram showing the usage of the system for loading a model based set of patient problems for use in a clinical application according to invention principles.

A flow diagram detailing the use of system 10 for loading a model based set of patient problems for use in a clinical application is shown in FIG. 3. In step 310, a patient problem is be loaded into a model stored in repository 20 within system 10. In response to loading a model, in step 310, system 10 in step 320, automatically decomposes a patient problem name associated with a particular patient problem into corresponding patient problem attributes which define the meaning of the patient problem name in the manner discussed above with respect to FIG. 1. These patient problem attributes are the judgment, client, focus, and patient problem likelihood terms. In step 330, system 10 matches the decomposed patient problem attributes to the patient problem attributes of previously defined patient problems which are stored in repository 20 of system 10 by comparing data values in attribute data fields and attribute property data fields with data values stored in repository 20 and which correspond to previously defined patient problem data. Step 335 queries whether or not a match is present during the comparison made in step 330. If the patient problem attributes match, the received patient problem is flagged as a duplicate in step 340 and system operation continues at step 360. In the event that the patient problem attributes of the decomposed patient problem name do not match with attributes of already stored and defined patient problems, System 10 automatically adds a record comprising a previously unentered patient problem name and any associated attributes in step 350. The system operation continues at step 360 and system 10 repeats the operation detailed in steps 310-350 for the remaining patient problem names loaded into system 10. When the process is complete for patient problems in step 360, step 370 allows a user or system 10 to specify attribute properties that correspond to the patient problem attributes for each patient problem. Upon completion of step 370 for loaded patient problems, step 380 indicates that the model-driven patient problem set is ready for use in a particular clinical application.

Figure 4:
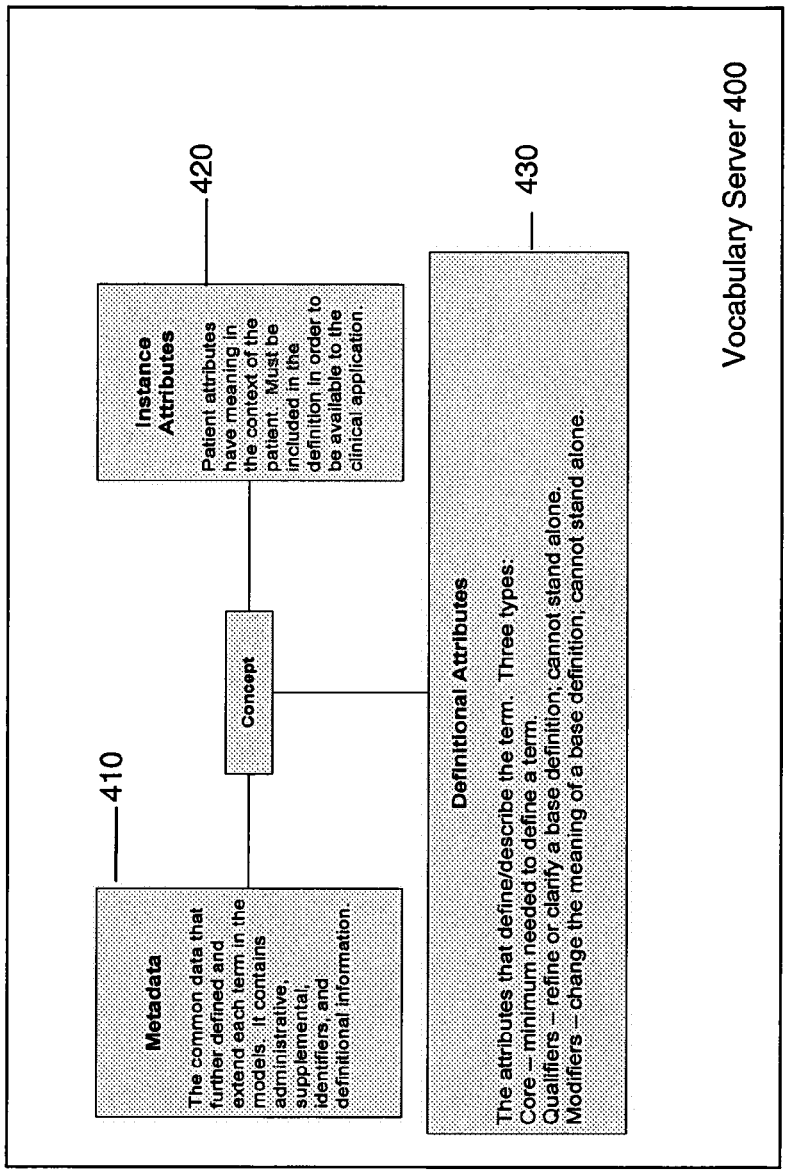
FIG. 4 is a block diagram detailing the setup and interaction of metadata and attributes within the model according to invention principles.

The structure of an exemplary patient problem concept is shown in FIG. 4. An individual patient problem concept is created using a vocabulary server 400 which defines key attribute values and properties that describe a respective patient problem. The concept and supporting structure, referred to as a definition instance, are created using and stored in vocabulary server 400. A particular concept may be defined as the patient problem as a whole, including associated attributes and attribute properties. A clinical application, for example a patient record updating system, searches for and uses a definition instance in the creation of a patient instance associated with the patient problem. The patient instance is defined by the definition instance and includes additional attribute values and properties that are applicable to describe a patient phenomenon. Clinical applications facilitate storage of a patient instance in a patient record of the particular patient.

Attributes, as shown in FIG. 4, include metadata 410, instance attributes 420, and definitional attributes 430. Attributes of a patient problem model direct operation of the clinical application, in this case the patient record update system, and corresponding user interface presented to an operator of the clinical application. Since an individual clinical application uses a common patient problem model provided by system 10, an individual clinical application is provided with a standard and consistent set of definitions from the central vocabulary server 400. Attributes also include attribute properties which are data values associated with respective patient problems that provide data describing desired application behavior associated with a specific attribute. Generally, these properties exist to serve the purpose of business logic control (e.g., duplicate checking) or user interface (e.g., display in a clinical application).

Patient instance attributes 420 and definitional attributes 430 are included in the models to support data-driven applications. Definitional attributes 430 describe a patient problem independent of the context in which they may be used. Definitional attributes are further divided into core attributes, qualifiers, and modifiers. Core attributes are required attributes which define a concept within a patient problem and are part of a pre-coordinated term. Qualifiers act to refine or clarify a base definition represented by core or other definitional attributes, such as severity, location, and time. Qualifiers may be single or multiple definitional attributes, as well as a pre-coordinated concept. Qualifiers terms are not required and do not function without the core attributes. Modifiers may change the meaning of a base definition, but also do not function without the core attributes.

Patient instance attributes have meaning in relation to, and in the context of a specific patient. The specific purpose of patient instance attributes is to direct the operation of the user interface, which is the point where data is collected. Patient instance attributes also include allowable value sets and characteristics of definitional attributes which serve to drive the application operation and corresponding user interface.

Metadata attributes are common data which further define and extend the concepts, or patient problems, in the models. Each patient problem, patient problem attribute, and patient problem attribute property is created as an individual concept within the general vocabulary server. Metadata may contain administrative, supplemental, identifier, and definitional information. Administrative information includes the source, version, status, create date/time, create user id, change data/time, change user id, review date/time, review user id, review comment, approval date/time, approval user id, and approval comment. Supplemental information includes a synonym or external reference value that correlates with at least one other element of patient problem data. Definitional information includes a concept type identifier, concept name, description, and text/text type. Metadata attributes advantageously enable system expansion to allow later deployed clinical applications to interface with System 10 and utilize the model of patient problems to facilitate patient specific data collection and/or workflow modification of a healthcare worker tasked with providing a healthcare service to the particular patient using the application.

System 10 is able to create and/or decompose patient problem data. Patient problem data includes data representing patient problem names. Patient problem name data includes a plurality of descriptor fields that are used to provide a common consistent set of definitional terms useable by multiple systems in a healthcare enterprise. Patient problem name data is generated by embedding data in descriptor attribute data fields in a particular sequence. Exemplary data structures for patient problem name data are shown in FIGS. 5A-5F. A pre-coordinated patient problem is defined as a patient problem statement, for example, Skin Integrity Impairment, or Anxiety. The individual meaning of the statement is defined by a unique combination of associated attribute values defined in particular fields. An individual patient problem statement name may be construed consistently using rules or attributes that allow the name to be composed in a specific sequence.

Figure 5A:
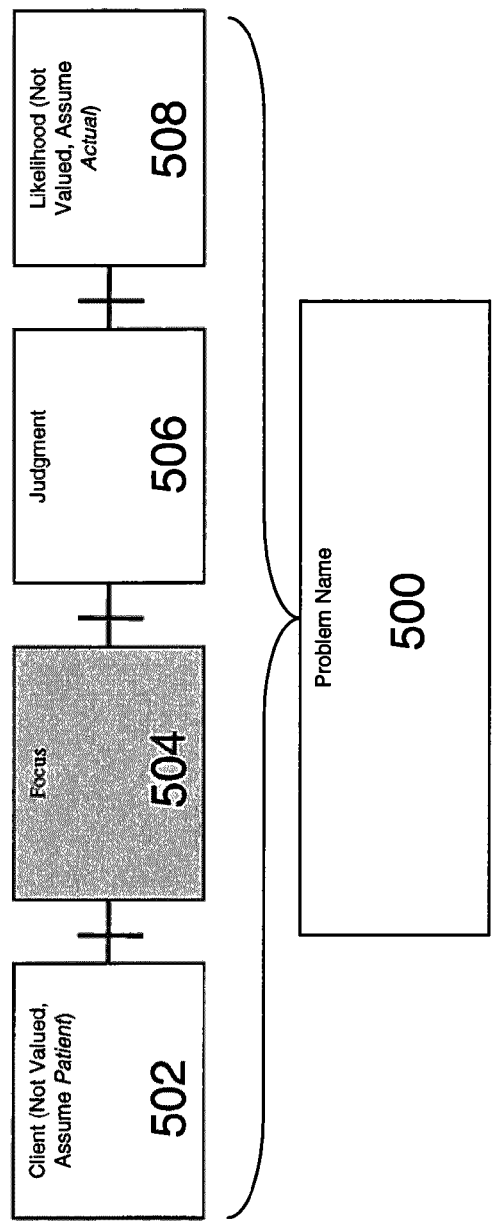
FIGS. 5A-5F shows the structure of a patient problem name according to invention principles.

FIG. 5A shows an exemplary structure of a patient problem name 500 and its associated attribute terms in respective data fields 502-508. Attribute data fields associated with a patient problem name include a client field 502, focus field 504, judgment field 506, and likelihood term 508. A data value in the focus term 504 is a term identifying the first word in the patient problem name 500, except in certain circumstances which are discussed below. Judgment term 506 is the second word in patient problem name 500. Patient problem likelihood term 508 is the third word in patient problem name 500, except in certain circumstances which are discussed below. Client term 502 is by default set to "patient," and does not appear in patient problem name 500 except in certain circumstances which are discussed below.

Figure 5B:
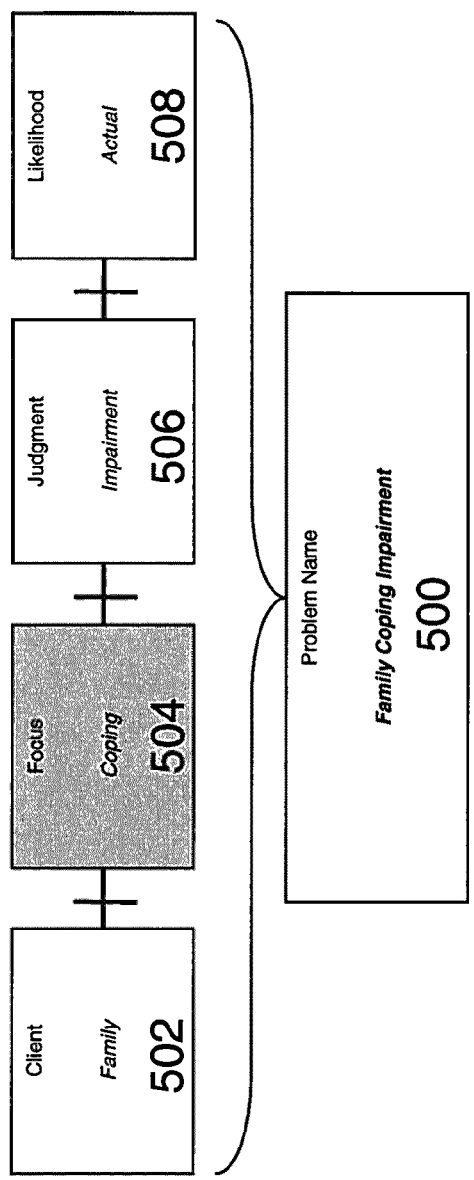

FIG. 5B is an exemplary structure of patient problem name 500 defined as "Family Coping Impairment". Patient problem name 500 in FIG. 5B is generated from data set in attribute fields 502-508. The values of attribute fields 502-508 are as follows: (a) client field 502 is set to "Family"; (b) focus field 504 is set to "Coping"; (c) judgment field 506 is set to "Impairment"; and (d) likelihood field 508 is set to "Actual". The resulting patient problem name is derived from fields 502-508 as discussed above and is able to be processed by System 10 as "Family Coping Impairment". In this example, the value of the client field is not equal to "patient," and thus appears first in the patient problem name 500. Additionally, as likelihood field 508 is set to "Actual," this value does not appear in patient problem name 500.

Figure 5C:
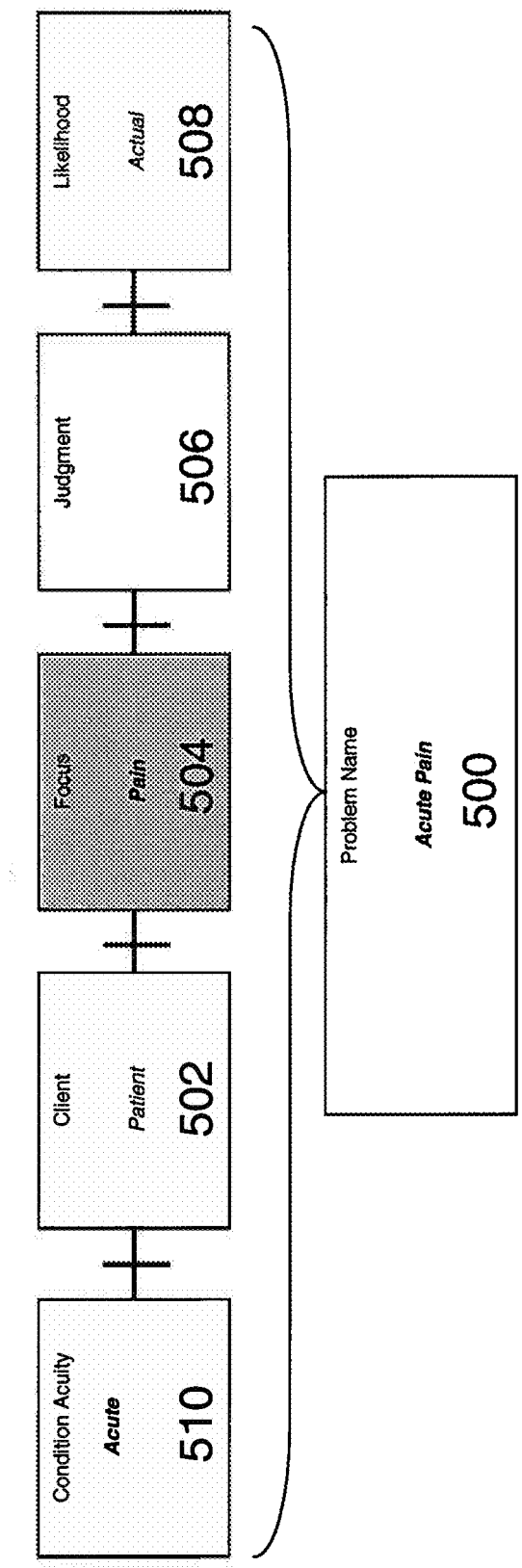

FIG. 5C is an exemplary structure of patient problem name 500 defined as "Acute Pain". Patient problem name 500 in FIG. 5C is generated from data set in attribute fields 502-510. The values of attribute fields 502-510 are set as follows: (a) client field 502 is set to "Patient"; (b) focus field 504 is set to "Pain"; (c) judgment field 506 is set to "None"; (d) likelihood field 508 is set to "Actual"; and (e) condition acuity field 510 is set to "Acute". The resulting patient problem name is derived from fields 502-510 as discussed above and is able to be processed by System 10 as "Acute Pain". In this example, the judgment, client, and likelihood fields are set to their default values and do not appear in the resulting patient problem name 500. Additionally, condition acuity field 510 appears and is set to "Acute," and thus appears first in the patient problem name 500.

Figure 5D:
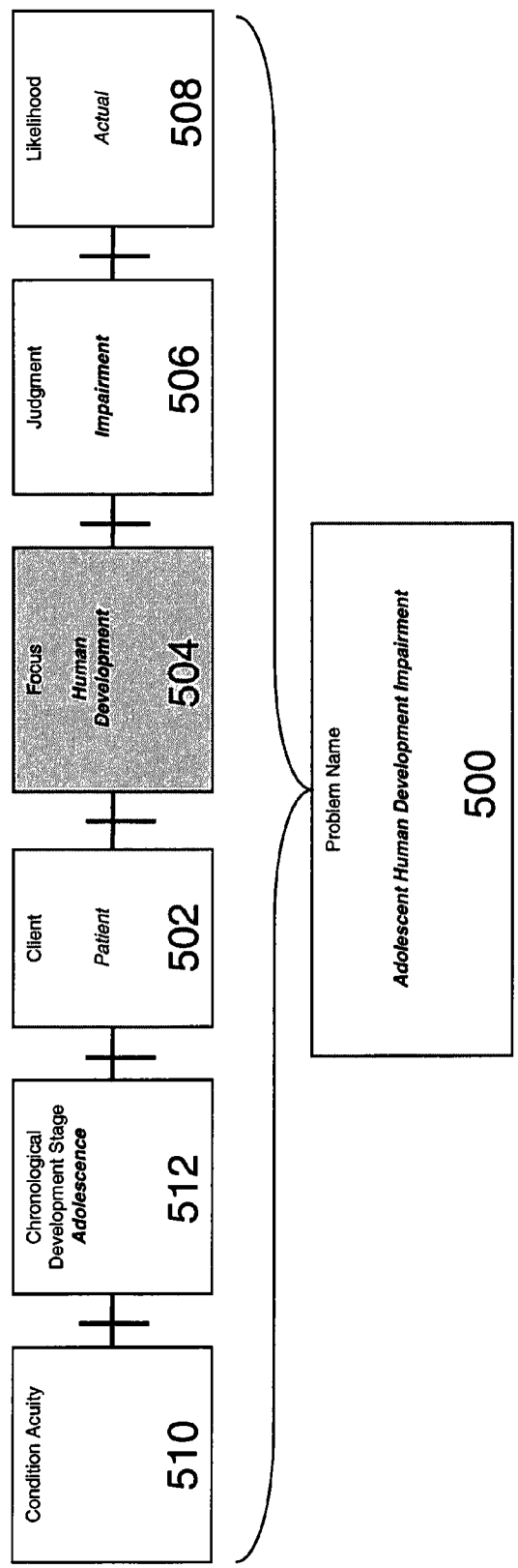

FIG. 5D is a further exemplary structure of patient problem name 500 defined as "Adolescent Human Development Impairment". Patient problem name 500 in FIG. 5C is generated from data set in attribute fields 502-512. The value of attribute fields 502-512 are set as follows: (a) client field 502 is set to "Patient"; (b) focus field 504 is set to "Human Development"; (c) judgment field 502 is set to "Impairment"; (d)

likelihood field 508 is set to "Actual"; and (e) chronological development stage 512 is set to "Adolescence". The resulting patient problem name is derived from fields 502-512 as discussed above and is able to be processed by System 10 as "Adolescent Human Development Impairment". In this example, the client and likelihood fields are set to their default values and do not appear in the resulting patient problem name 500. In addition, focus field 504 may be changed to remove any redundancy from patient problem name 500. Since chronological development stage field 512 is active, it appears first in the patient problem name 500.

Figure 5E:
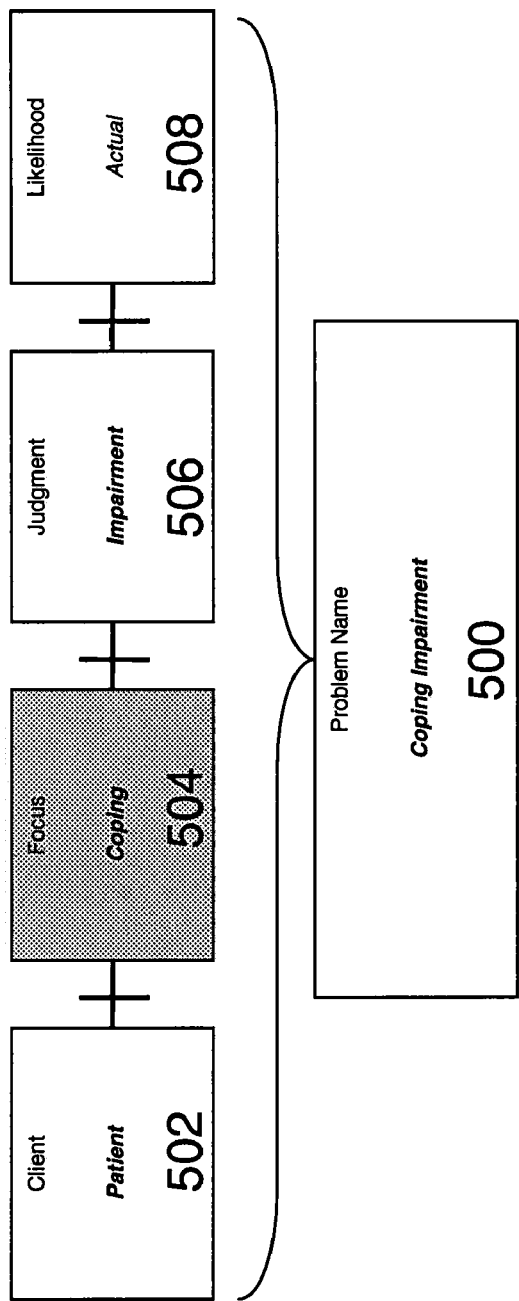

FIG. 5E shows another exemplary structure of patient problem name 500 and its associated attribute terms. Shown herein, the value in likelihood term 508 is set to "Actual". "Actual" is the default setting for likelihood field 508. In this case, the word "actual" does not appear in patient problem name 500. Thus, patient problem name 500 is processed by System 10 as "Coping Impairment".

Figure 5F:
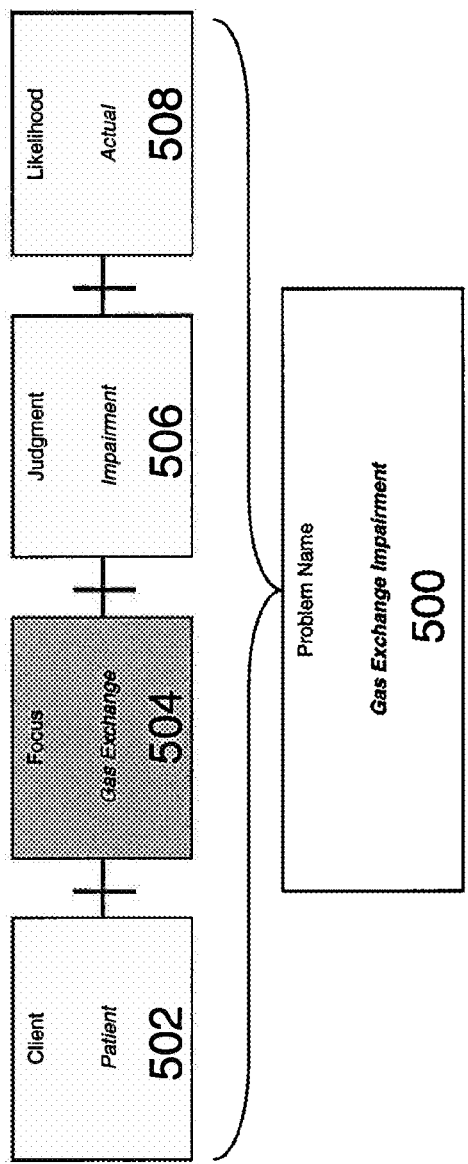

FIG. 5F is another exemplary structure of patient problem name 500 and its associated attribute terms. Shown herein, the value of client field 502 is set to "Patient". "Patient" is the default setting for client field 502. In this case, the word "patient" does not appear in patient problem name 500. Thus, patient problem name 500 is processed by System 10 as "Gas Exchange Impairment".

Figure 6:
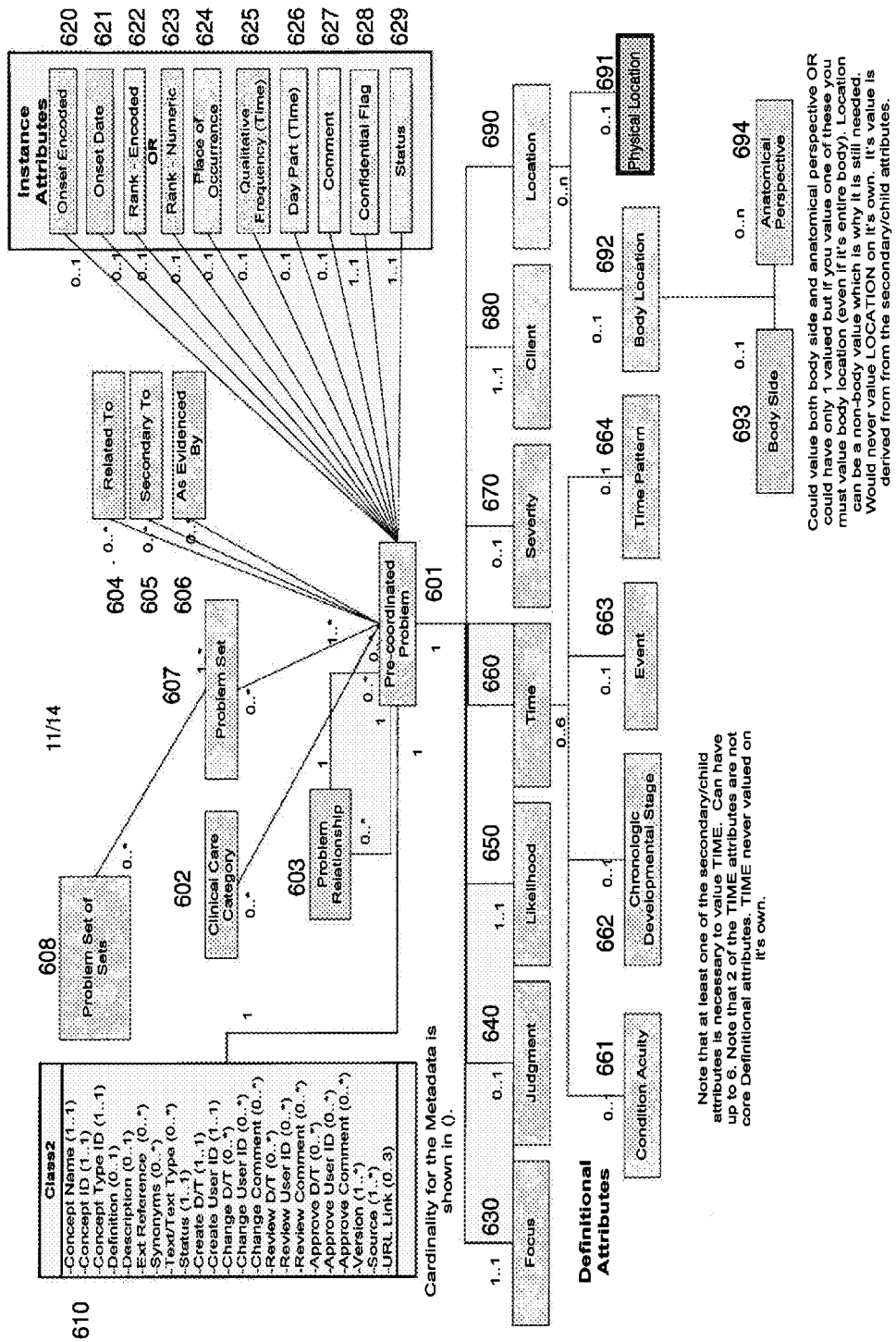
FIG. 6 is a block diagram showing the hierarchy and interrelationships of elements of a patient problem according to invention principles.

An exemplary guideline for parameter value sequencing in a pre-coordinated problem name 601 is shown in FIG. 6. In relation to the parameter values, FIG. 6 depicts the hierarchy, as well as the interrelationships that exist within a patient problem and its attributes or components. Data representing patient problem name 601 that is stored and processed by System 10 includes definitional core attributes. Definitional core attribute data values are associated with a particular patient problem definition instance and include focus term data 630, judgment term data 640, likelihood term data 650, and client term data 680. Focus term data 630 identifies the topic of attention (e.g., pain, knowledge deficit, or gas exchange). Judgment term data 640 describes the clinical opinion or determination about the actual or potential health problem or life process. This term may indicate positive (e.g., increase), negative (e.g., impairment), or neutral (e.g., not valued). Likelihood term data 650 describes the probable state of the topic of attention (e.g., actual or risk). Client term data 680 describes the target of care (e.g., patient, parent, or family). Additional attributes are also optionally defined by a user to provide further description of patient problem name data 601.

Patient problem name data further includes data representing a definitional modifier of a data value in a respective attribute data field. Definitional modifiers change the meaning of a base definition (e.g., adding negation or "family history of" to a patient problem name). In certain instances the value in judgment term field 640 qualifies as a definitional modifier attribute since it is involved in changing the base definition of a patient problem name. Patient problem name data further includes data representing a definitional qualifier of data in a particular attribute field. Definitional qualifier data values serve to further clarify and define a base definition of a value in a particular data field.

A further attribute field associated with patient problem name data 601 is a time attribute data field 660. The value of time attribute data field 660 is derived from values set in attribute sub-fields 661-664. The subfields that include values representing time attribute data include at least one of: condition acuity data value 661, chronologic developmental stage data value 662, event data value 663 and time pattern data value 664. Condition acuity data value 661 describes a determination derived from duration, and/or number of occurrences, and/or observations, and/or findings of a particular patient condition (e.g., acute or chronic). Chronologic developmental stage data value 662 describes human biological development, expressed as qualitative, age-related physical development stages (e.g., adolescence). Event data value 663 describes a situation with specific characteristics, or something that can take place, such as an occurrence (e.g. admission). Time pattern data value 664 describes determination of whether the related object occurs in an uninterrupted fashion (e.g., continuous, intermittent).

Patient problem name data 601 further includes a severity attribute data field 670 including a data value identifying the subjective measure of the relative, and not quantitative, degree of the patient problem (e.g., mild, moderate, severe) valued in focus data field 630.

Location attribute data field 690 of patient problem name 601 includes data identifying a setting where an event, entity or process occurs or is located. However, the data value in location data field 690, similar to the data value in time data field 660, is derived from values set in attribute sub-fields 691-694. The sub-fields that include values representing time attribute data include at least one of: physical location data field 691 and body location data field 692. Physical location data field 691 identifies a particular potion of space having substance or material existence (e.g., workplace). Body location data value 692 identifies a bodily system, structure, region, or any component parts thereof. Body location 692 is further characterized by attribute data fields for body side 693 and anatomical perspective 694. A value in body side data field 693 describes the side(s) of the body identified by location with respect to a center (e.g., left, right, bilateral). A value in anatomical perspective data field 694 describes a location in relation to sagittal, coronal, oblique, and transverse plans of the body (e.g., anterior, posterior, inferior). These attributes advantageously provide patient specific information that is utilized by a clinical application for generating a request for healthcare to be provisioned by a worker or for use in updating a task schedule of a healthcare professional to improve a level of patient care, for example.

Patient problem name data 601 further includes clinical care category data field 602 which include a data value identifying a category for grouping similar patient problems. This data value is used by a clinical application to visually organize and categorize the components of patient problem name data on a user interface when presenting patient problem name data to a healthcare provider.

Problem relationship data field 603 is associated with patient problem name data 601 and identifies when two or more phenomena are connected or associated, such that the behavior of one impacts the behavior of another and vice versa. Data values identifying relationships between problems are set in problem relationship data field 603. If a value appears in field 603, the value represents three types of relationships. A first data value is defined by "Related To" data field 604, which identifies a phenomenon that is connected or associated with a given problem. The onset and resolution of a problem is impacted by the onset and resolution of another problem. Thus, the status of one problem impacts the status of another problem. For example, Alteration in Fluid/Electrolyte Balance Impairment related to Cardiac Output Decrease,
Activity Intolerance related to Fatigue,
Activity Intolerance related to Cardiac Output Decrease,
Nausea related to Bowel Elimination Impairment A second data value is defined by "Secondary To" data field 605, which identifies a phenomenon that is dependent on or incidental to the original or primary problem. A problem is directly caused by another phenomenon, such that resolution of the causative problems, with other conditions held constant, will resolve the existence of another problem. For example, Septicemia secondary to Surgical Wound Infection.

Skin Integrity Impairment Alteration secondary to Physical Mobility Impairment

A third data value is defined by "As Evidenced By" data field 606, which identifies an indication that makes a patient problem evident. This term may take the form of an observation of a pre-coordinated problem. The observation would be signs or symptoms that tend to prove or disprove something, such as supporting documentation. The pre-coordinated problem would be the existence of one phenomenon as a predictor that another phenomenon will or may occur. The interventions applied to resolve one phenomenon enable the resolution of another phenomenon. For example, Gas Exchange Impairment as evidenced by increased respiratory rate, shortness of breath, dyspnea on exertion.

Cardiac Output Decrease as evidenced by peripheral edema and Mental Status Alteration Problem set data field 607 is associated with patient problem name data 601 and represents a customer configurable group of similar patient problems. Data values in problem set data field 607 are used by System 10 during a search for an assignment of patient problems. Examples include:

Mechanical Ventilation problems
        Injury Risk
        Cardiac Output Decrease
        Airway Clearance Impairment
        Physical Mobility Impairment
        Anxiety
        Infection Risk
    Alzheimer's Disease
        Condition Impairment
        Ability to Bathe Self Impairment
        Ability to Dress Self Impairment
        Ability to Toilet Self Impairment
        Injury Risk
        Coping Impairment
    Shock
        Cardiac Output Decrease
        Anxiety Problem set of sets data field 608 is associated with patient problem name 601 and represents a customer configurable grouping of patient problems for a 'folder' type structure. This feature is used for browsing by System 10, but not searching, when a problem is assigned. Examples include:

Body system approach would include groups/folders for:
        Cardiovascular
        Respiratory
    Clinical classifications approach (e.g., Nursing Intervention Classification—NIC, Nursing Outcomes Classification—NOC, Clinical Care Classification—CCC schemes) would include groups/folders for:
        Activity—Exercise
        Nutrition—Metabolic
        Cognitive
        Coping
    Clinical specialty approach would include groups/folders for:
        Pediatrics
        Critical Care
        Medical/Surgical A further attribute data field attribute used to characterize and describe patient problem data 601 includes patient instance attribute data fields 620-629. Data values set in fields 620-629 are data values that have meaning in the context of a specific patient. The data values in fields 620-629 are included in a patient problem model to drive operation of the end user interface where data is collected by a healthcare professional. Patient instance attributes include onset date data field 620 and onset encoded data field 621. Onset date data field 620 identifies the date a particular condition started. Onset encoded data field 621 identifies an inexact recording of condition start (e.g., 2 weeks ago, adolescence).

Additional patient instance attribute data fields include rank-encoded data field 622 and rank-numeric data field 623 which represent an encoded and numeric value, respectively, that indicates relative importance of a particular patient problem name data 601 (e.g., high, medium, low). Rank-encoded data field 622 and rank-numeric data field 623 represent the priority of patient care based upon a particular patient problem name. In exemplary operation, a clinical application receiving patient problem name 601 including attribute data values in fields 622 and/or 623 automatically ranks the particular patient problem name associated with fields 622 and 623 with other patient problems already stored in repository 20 in order to facilitate a priority of care ranking for all problems for a particular patient.

Place of occurrence data field 624 includes data identifying the client location where a patient problem took place or started (e.g., home).

Qualitative frequency data field 625 includes data identifying the subjective, and not quantitative, report of occurrences of events or activities within a given period of time (e.g., always, frequent, occasional, rarely).

Day part data field 626 includes data identifying the part of the day an event or activity occurred (e.g., morning, afternoon).

Comment data field 627 includes data entered by a clinician to further describe the problem instance for a particular patient (e.g., in initial implementations, it provides a way to record an etiology if known or a related problem or condition)

Confidential flag data field 628 includes data indicating whether particular information is deemed confidential. In an exemplary operation, if confidential flag data field 628 includes data, then the patient problem with which it is associated may be restricted from access from certain individuals in a healthcare environment.

Status data field 629 includes data identifying a state documented at a point in time. For example, for a problem status, the value could be: active, inactive, resolved, and erroneous.

Metadata attributes 610 are common concepts in the model. They provide additional information to describe the concept. Concept name provides a meaningful, unambiguous text string to represent a concept. The concept name needs to be individual within concept types.

Concept ID is a name used by applications for processing. An example of a concept ID for the unit of measure concept minutes is MIN. Applications recognize and correctly process minutes because the applications recognize the concept ID MIN.

Concept type defines the term type for a specific term. An individual term may be associated with more than one term type. For example, a term with the name WBC may operate as a service as well as an observation.

Description provides text describing or defining a concept.

External references are mechanisms used to associated external terminology and interface identifiers to concepts, as well as drive application logic. An external reference name is the name by which an entity, or other system, industry-standard terminology source, or content source, recognizes the concept.

Synonyms provide multiple names to be defined for one concept. This facilitates searching for a concept. A synonym is not used as the display name.

Text/TextType is text that may be any value appropriate in relationship to the text role code. The term text entity contains additional text about a specific concept and concept type.

Status indicates whether the concept is active or inactive.

Create D/T provides the date and time the concept was created.

Create user provides the user identifier or program of the concept creator.

Change D/T provides the date and time the term was most recently changed.

Change User ID provides the user identifier or program that last changed the concept.

Change Comment provides free text comments related to the revision.

Review D/T provides the date and time the term was reviewed.

Review User ID provides the user identifier of the user who last reviewed the concept.

Review Comment provides free text related to the review of this concept definition.

Approve D/T provides the date and time the concept was approved.

Approve User ID provides the user identifier of the user who approved the concept.

Approve Comment provides free text related to the concept approval.

Version provides a specific identifier for the concept version.

Source provides the source of concept description/definition.

URL link provides a reference or navigation that automatically brings the referred information to the user when a navigation element is selected by the user.

Figure 7:
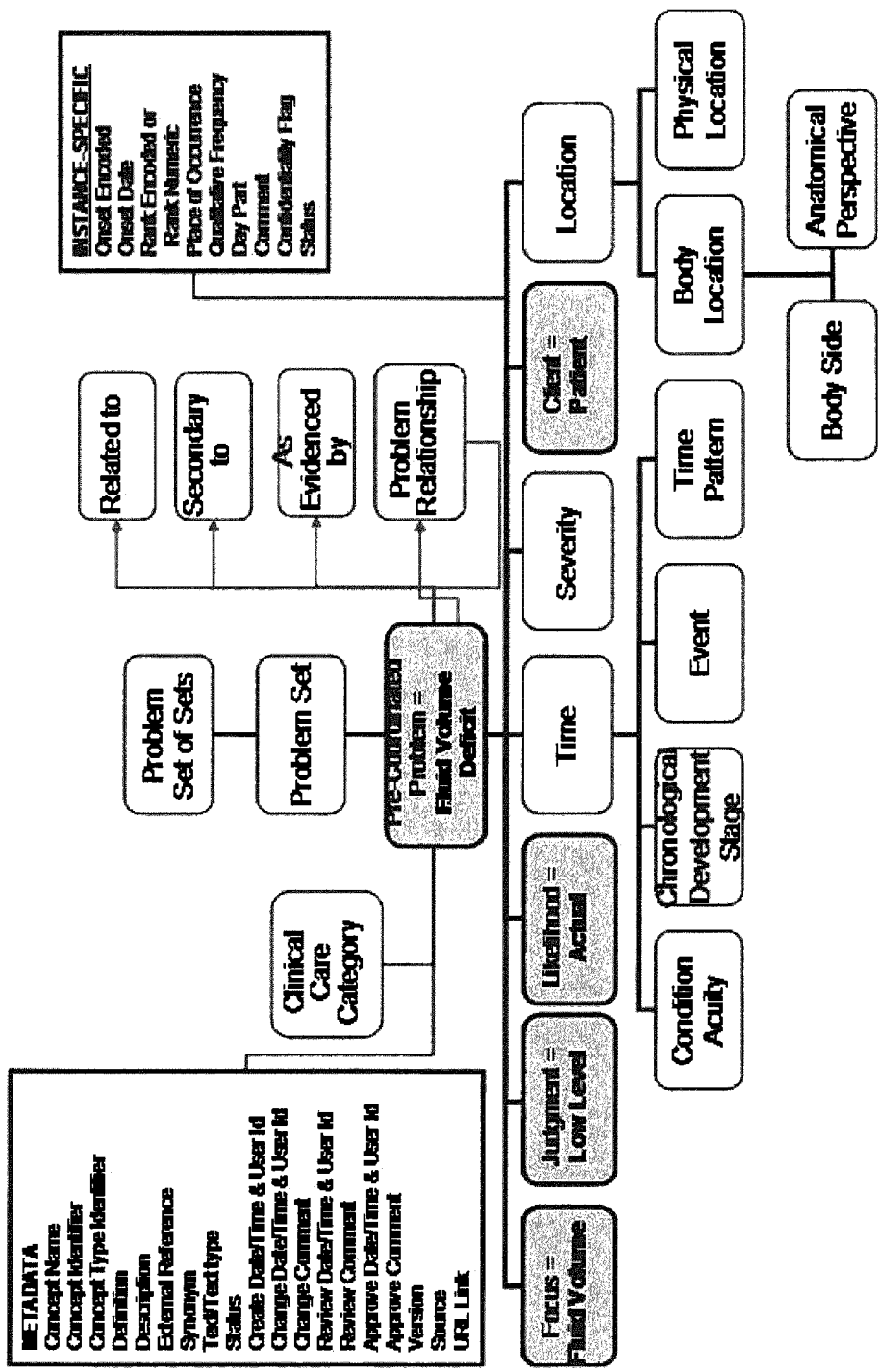
FIG. 7 is a block diagram showing one example of a patient problem name according to invention principles.
Figure 8:
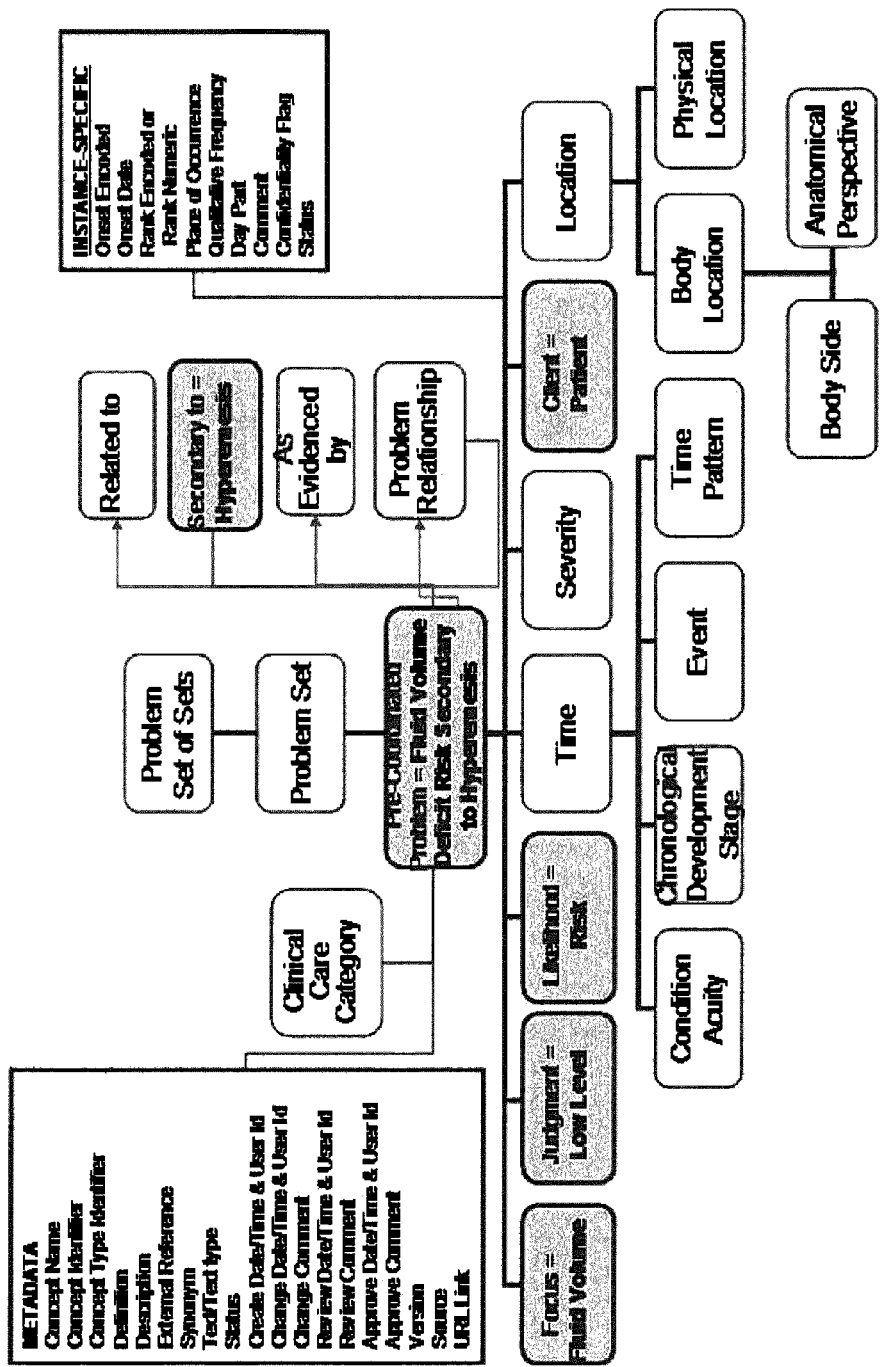

Two examples of how the patient problem definition model core attributes may be valued to create a patient problem definition instance are shown in FIGS. 7 and 8. The core attributes (focus term, judgment term, likelihood term and client term) that are a part of the fundamental definition of the patient problem instance have been valued. With respect to FIG. 7, the focus term is valued as "Focus=Fluid Volume", the judgment term is valued as "Judgment=Low Level", the likelihood term is valued as "Likelihood=Actual" and the client term is valued as "Client=Patient". Therefore, according to the predetermined naming rules discussed above with respect to FIGS. 5A-5F, the resulting expected outcome name is "Fluid Volume Low Level". Referring now to FIG. 8, the focus term, judgment term and client term core attribute values are set equal to those described with respect to FIG. 7. However, the value of the likelihood term is set as "likelihood=Risk". Additionally, a further attribute value, the "secondary to" attribute data field, also is valued. In FIG. 8, the "secondary to" attribute is valued as "Secondary to=Hyperemesis". Thus, the patient problem name defined by the model shown in FIG. 8 is "Fluid Volume Deficit Risk Secondary to Hyperemesis". The differences between FIGS. 7 and 8 stem from the expected problem name in FIG. 8 including a data value in attribute data field, patient problem likelihood, having a value of "risk" (FIG. 8) rather than "actual" (FIG. 7) as well as an additional attribute data field, the "secondary to" attribute, having a value in FIG. 8 and not in FIG. 7. Thus, it is demonstrated that simply changing the value of one core attribute (or adding a value to a further attribute data field) results in the meaning of the patient problem definition instance to be changed.

Attribute properties are properties that further describe patient problem attributes for use in particular clinical applications. For example, attribute data fields 620-694 in FIG. 6 each include at least one attribute property data field associated therewith. It should be noted that, any attribute data field associated with expected outcome name data may include at least one attribute property data field. Attribute property data fields are associated with respective clinical applications within a healthcare enterprise and data values in respective attribute property data fields are selectively useable by clinical applications directing the manner in which the clinical application handles and/or uses data in attribute data field with which attribute property data is associated. An individual clinical application that uses the patient problem model of system 10 uses its own individual attribute properties to account for behavioral differences and constraints within a particular clinical application since each clinical application has its own business and user interface characteristics. An individual attribute property defines some application behavior, either for vocabulary authoring or the clinical application itself. Table 1 illustrates exemplary attribute properties and that properties appropriate default setting recommendation. An individual attribute property is used based on clinical application requirements.

| Short Name | Long Name | Definition |
| --- | --- | --- |
| Dup Check | Duplicate Checking | This duplicate check indicator defines whether the value for this Parameter will be included in clinical duplicate checking. If set to "Yes", this Parameter is used to check for duplicates when the patient problem is added to the patient and when the patient problem is added/revised in the vocabulary server and a default value is present. If the 'dup check' parameters are the same it is considered a duplicate. If ANY ONE of these 'dup check' parameters is different it will not be considered a duplicate. It is recommended that the default is set equal to "Yes" for any Parameter that is included in the definition instance model. |
| Req to Create | Required to Create Term | This indicator defines whether the model builder needs to enter a default value for this Parameter when a patient problem is added or revised. Any Parameter that needs to have a default value to create the patient problem should have this property set to Yes. |
| Allow Val Set | Allowable Value Set | The Allowable Value Set constrains the default values that may be entered for this Parameter when the patient problem is added/revised in the vocabulary server, as well as in the clinical application. |
| Dflt Val | Default Value | The Default Value defines the Value that is automatically assigned for the Parameter. A Default Value can be entered if the data type of the Parameter is numeric, encoded or date offset. This value needs to be a member of the Allowable Value Set. |

| Short Name | Long Name | Definition |
|---|---|---|
| | | It is beneficial to use this option if the default value is selected a high percentage of time. |
| UOM | Unit of Measure | The Unit of Measure is given a value if the Parameter accepts numeric or date offset values. The Unit of Measure is available for display with numeric values. It is also available for the clinical application to correctly set a default date/time based on the date offset value. |
| Decimal Places | Decimal Places | The Number of Decimal Places defines the number of digits to the right of the decimal that may be entered for the default value. This is valid for Parameters that accept numeric values. |
| Max No of Vals | Maximum Number of Values Allowed | The Maximum Number of Values Allowed determines the number of values that may be entered in the clinical application for a Parameter. The default value is set to 1 but can be changed to a number greater than 1 for those Parameters where it makes sense (e.g. Anatomical Perspective). |
| Req in Pt App | Required in Patient Application | Required in Patient Application indicates that the clinical application requires a value for the Parameter. There are 2 ways that the value can be set: the value can be provided when the definition is created for the patient problem or the end user clinician can provide a value. Any Parameter with a cardinality of 1:1 in the model should have this property to Yes. |
| Allow Free Text | Allow Free Text | Allow Free Text defines whether the patient application process allows a free text string to be entered for a Parameter that accepts encoded values. |
| Max Len | Maximum Length | Maximum Length determines the maximum number of characters that may be entered in the patient application for a Parameter that accepts free text value (Allow Free Text = Yes). |
| Set Mem Override | Set Member Override | Set Member Override defines whether the default value for this Parameter may be overridden when the related patient problem term is a member of a Plan of Care. |
| Dsply in Pt App | Display in Patient Application | Display in Patient Application defines whether the default value for this Parameter is displayed in the patient application. This property is set to "No" if there is a Parameter value that does not provide value to the clinician at the point in time of patient problem entry. For example, the Focus, Judgment, Likelihood and Client Parameters typically have a value assigned, and are not allowed to change when the patient problem is assigned to a patient. There is no need to display the values to the end user since they are represented in the patient problem name. For example, a value may not be required for Chronological Development Stage for a patient problem definition. The institution would like the clinician to enter a value for Chronological Development Stage. Set Display in Patient Application to Yes to display the prompt and the Allowable Value Set. The discrete values are available to the clinical application for secondary data use (e.g. Rules, Workflow) |

Table 1

Attribute Property Data Values

Figure 9:
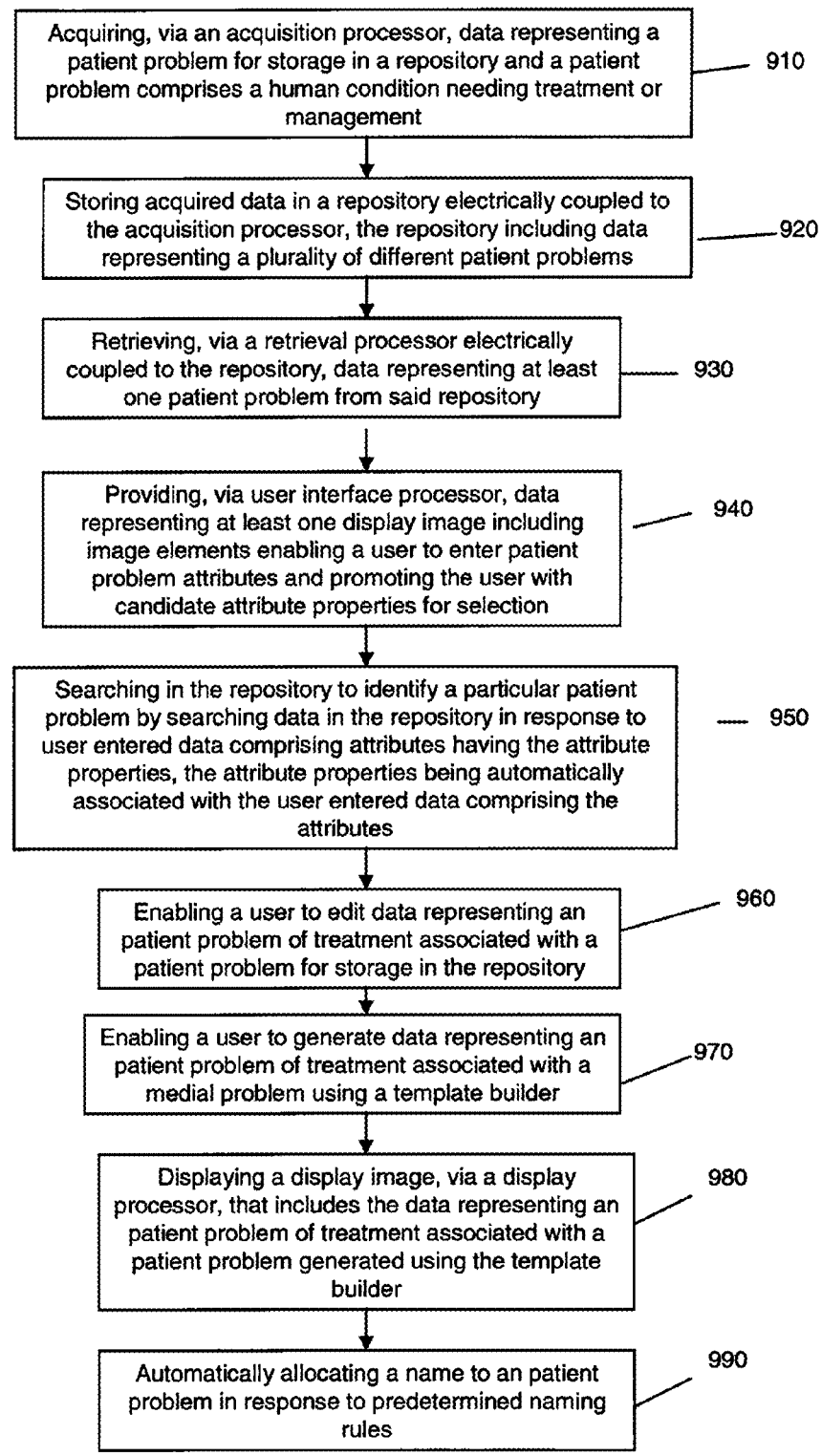
FIG. 9 is a flow diagram detailing system operation according to invention principles.

FIG. 9 is a flow diagram detailing operation of patient problem data system 10 shown in FIG. 1. Patient problem data system 10 stores data representing a plurality of different patient problems for use in providing healthcare to a patient. In step 910, an acquisition processor acquires data representing a patient problem for storage in a repository and a patient problem comprises a human condition needing treatment or management. Acquisition processor, in one embodiment, acquires data representing a patient problem compatible with the attribute properties. In a further embodiment, the data representing a patient problem acquired by the acquisition processor is converted by a data converter, to be compatible with the attribute properties enabling storage thereof.

The acquired data is stored, in step 920, in a repository. The repository is electrically coupled to the acquisition processor and includes data representing a plurality of different patient problems. An individual patient problem has a problem name and is characterized by problem attributes. The problem attributes include a focus term indicating a topic of the patient problem, a patient problem likelihood term indicating an assessment of likelihood of the associated corresponding patient problem and a client term indicating at least one target person for care. Problem attributes further include data representing at least one of (a) patient condition acuity, (b) chronologic development stage of a patient condition, (c) an indication of a clinical event (d) an indication of a time pattern associated with a patient condition, (e) an indication of review action needed in treatment of a patient condition, (f) an indication of approval action needed in treatment of a patient condition and (g) a judgment term indicating a clinical opinion concerning a patient problem. Data representing a clinical opinion indicates at least one of, (a) a positive, (b) a negative and (c) a neutral, status of a patient problem.

An individual problem attribute has a plurality of attribute properties determining how a problem attribute is represented. The attribute properties associated with the attributes include a format attribute property indicating a format constraint of a problem attribute and a content attribute property indicating a content constraint of a problem attribute. The format attribute property comprises at least one of, (a) maximum character length of an attribute, (b) a unit of measure of an attribute and (c) a number of decimal places an attribute has. The content attribute properties comprises at least two of, (a) an allowable value set of an attribute, (b) a default value of an attribute, (c) a maximum number of values allowed for an attribute and (d) an indication free text entry is allowed for user entry of data representing an attribute. The attribute properties further include processing attribute properties that includes at least one of, (a) an indication an attribute is to be processed in performing a check for a duplicate problem (b)

an indication a default value is required for an attribute, (c) an indication an attribute is required for use by an executable clinical application (d) an indication an attribute is displayed in a display image associated with said executable clinical application, (e) an indication an attribute value may be overridden.

The repository further associates an individual problem with metadata attributes including at least one of, a problem identifier, external references and synonyms. Metadata attributes alternatively include data identifying who created, changed or reviewed patient problem information.

A retrieval processor, electrically coupled to the repository, retrieves data representing at least one patient problem from the repository in step 930. In step 940, a user interface processor provides data representing at least one display image including image elements enabling a user to enter patient problem attributes and for prompting the user with candidate attribute properties for selection. The at least one display image includes image elements for prompting the user with candidate attributes for selection for inclusion as patient problem attributes or patient problem attribute properties. User interface processor alternatively provides data representing at least one display image enabling a user to enter at least one of genomic and proteomic data associated with a particular patient. In response thereto, system provides the user with candidate attribute properties for selection in response to the at least one of patient specific genomic and proteomic data.

In step 950, a data processor searches data in the repository to identify a particular patient problem by searching data in said repository in response to user entered data comprising attributes having the attribute properties, the attribute properties are automatically associated with the user entered data comprising the attributes. The searching in step 950 further includes searching data in the repository to identify at least one of, (a) a candidate plan of care, (b) a treatment and (c) a diagnosis, associated with a particular patient problem by searching data in the repository in response to user entered data identifying patient problem attributes having the attribute properties. Alternative, the search step 950 includes searching data in the repository in response to patient-specific genomic and/or proteomic data to identify at least one of, (a) a candidate plan of care, (b) a treatment and (c) a diagnosis, associated with a particular patient problem by searching data in the repository in response to user entered data identifying patient problem attributes having the attribute properties An edit processor, in step 960, enables a user to edit data representing a patient problem for storage in the repository. A template builder processor, in step 970, enables a user to generate data representing a patient problem and a display processor generates data representing at least one display image including the data representing a patient problem. In step 990, a name processor automatically allocates a name to a patient problem response to predetermined naming rules.

Referring back to FIG. 1, a user of System 10 is able to selectively create and modify patient problem name data for a particular patient problem. A user selectively sets data values for any of the plurality of attribute data fields described in FIG. 6 and attribute property data values described in Table 1. System 10 also automatically acquires data representing patient problem names for particular healthcare activities. The acquired patient problem name data includes terms that correspond to at least one attribute data field identifying a meaning of the term. Also included are data values for predetermined attribute data fields that are used to further describe the patient problem. The system 10 searches repository 20 for instances of terms, and if none are found, automatically creates a patient problem record. The record created in repository 20 includes all attribute data fields associated with the received patient problem data. The system 10 automatically populates the attribute data field in the created record with corresponding attribute data associated with the acquired patient problem data. Once stored, system users can selectively modify data values stored in the record. Alternatively, users are able to add additional attribute fields and set data values for the added fields. These added fields are used by clinical applications for driving operation of a particular application and/or identifying how data associated with the clinical application is to be presented to an end user. Thus, system 10 advantageously enables consistent, model-driven application and user interface behavior associated with the collection, translation, and interpretation of patient problems. System 10 includes a model structure including detailed attributes associated with patient problems and supplemental information associated with patient problems that is necessary to drive application behavior.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. A patient problem data system for storing and retrieving data representing a plurality of different patient problems for use in providing healthcare to a patient, comprising:

at least one computer system including, an acquisition processor for acquiring data representing a patient problem for storage in a repository and a patient problem comprises a human condition needing treatment or management;

at least one repository, electrically coupled to said acquisition processor, including data representing a plurality of different patient problems and an individual problem has a problem name and is characterized by problem attributes and an individual problem attribute has a plurality of attribute properties determining how a problem attribute is represented, said problem attributes including, a focus term indicating a topic of the patient problem, a patient problem likelihood term indicating an assessment of likelihood of the associated corresponding patient problem and a client term indicating at least one target person for care, said attribute properties including, a format attribute property indicating a format constraint of a problem attribute and determining formatting or presentation of said problem attribute and a content attribute property indicating a content constraint of said problem attribute and determining modification of said problem attribute; and a retrieval processor, electrically coupled to said at least one repository, for retrieving data representing at least one patient problem from said at least one repository and communication of said problem attributes to a destination system for determining the manner in which the destination system uses the patient problem data.

2. A system according to claim 1, wherein
said at least one repository includes a plurality of individual sets of problem attribute properties associated with a corresponding plurality of individual clinical applications using the attribute properties and including
a user interface processor for providing data representing at least one display image including image elements enabling a user to enter patient problem attributes and for prompting said user with candidate attribute properties for selection.

3. A system according to claim 2, wherein
said at least one display image includes image elements for prompting said user with candidate attributes for selection.

4. A system according to claim 1, wherein
said acquisition processor acquires data representing a patient problem compatible with said attribute properties for storage in said repository and
data values of attribute properties provide operating instructions to a respective clinical application driving operation of the clinical application and determining the manner in which the clinical application uses the patient problem data.

5. A system according to claim 1, including
a data converter for converting data representing a patient problem acquired by said acquisition processor to be compatible with said attribute properties for storage in said repository.

6. A system according to claim 1, including
a data processor for searching data in said repository to identify a particular patient problem by searching data in said repository in response to user entered data comprising attributes having said attribute properties, said attribute properties being automatically associated with said user entered data comprising said attributes.

7. A system according to claim 1, wherein
said data processor searches data in said repository to identify at least one of, (a) a candidate plan of care, (b) a treatment and (c) a diagnosis, associated with a particular patient problem by searching data in said repository in response to user entered data identifying patient problem attributes having said attribute properties.

8. A system according to claim 1, wherein
said attribute properties include a format attribute property comprising at least one of, (a) maximum character length of an attribute, (b) a unit of measure of an attribute and (c) a number of decimal places an attribute has.

9. A system according to claim 1, wherein
said attribute properties include content attribute properties comprising at least two of, (a) an allowable value set of an attribute, (b) a default value of an attribute, (c) a maximum number of values allowed for an attribute and (d) an indication free text entry is allowed for user entry of data representing an attribute.

10. A system according to claim 1, wherein
said attribute properties include processing attribute properties comprising at least one of, (a) an indication an attribute is to be processed in performing a check for a duplicate problem and (b) an indication a default value is required for an attribute.

11. A system according to claim 1, wherein
said attribute properties include processing attribute properties comprising at least one of, (a) an indication an attribute is required for use by an executable clinical application and (b) an indication an attribute is displayed in a display image associated with said executable clinical application.

12. A system according to claim 1, wherein
said attribute properties include processing attribute properties comprising an indication an attribute value may be overridden.

13. A system according to claim 1, wherein
said problem attributes include medical condition acuity.

14. A system according to claim 1, wherein
said problem attributes include at least one of, (a) chronologic development stage of a medical condition, (b) an indication of a clinical event and (c) an indication of a time pattern associated with a medical condition.

15. A system according to claim 1, wherein
said problem attributes include an indication of review action needed in treatment of a medical condition.

16. A system according to claim 1, wherein
said problem attributes include an indication of approval action needed in treatment of a medical condition.

17. A system according to claim 1, wherein
said data representing a plurality of different patient problems comprises data representing names of patient problems and
including a name processor for automatically allocating a name to a patient problem in response to predetermined naming rules.

18. A system according to claim 1, wherein
said problem attributes include a judgment term indicating a clinical opinion concerning a patient problem.

19. A system according to claim 18, wherein
said clinical opinion indicates at least one of, (a) a positive, (b) a negative and (c) a neutral, status of a patient problem.

20. A system according to claim 1, including
an edit processor enabling a user to edit data representing a patient problem for storage in said repository.

21. A system according to claim 1, including
a template builder processor enabling a user to generate data representing a patient problem.

22. A system according to claim 21, including
a display processor for generating data representing at least one display image including data representing said patient problem generated using said template builder.

23. A system according to claim 1, wherein
said repository associates an individual problem with metadata attributes including at least one of, a problem identifier, external references and synonyms.

24. A system according to claim 1, wherein
said repository associates an individual problem with metadata attributes including data identifying who created, changed or reviewed patient problem information.

* * * * *